United States Patent
Prinderre (10) Patent No.: US 10,010,510 B2
(45) Date of Patent: Jul. 3, 2018

(54) ORAL PHARMACEUTICAL FORMULATION

(71) Applicant: SIEGFRIED AG, Zofingen (CH)

(72) Inventor: Pascal Christian Prinderre, Muespach (FR)

(73) Assignee: SIEGFRIED AG, Zofingen (CH)

( * ) Notice: Subject to any disclaimer, the term of this patent is extended or adjusted under 35 U.S.C. 154(b) by 0 days.

(21) Appl. No.: 14/889,009

(22) PCT Filed: May 6, 2014

(86) PCT No.: PCT/EP2014/059249
§ 371 (c)(1),
(2) Date: Nov. 4, 2015

(87) PCT Pub. No.: WO2014/180855
PCT Pub. Date: Nov. 13, 2014

(65) Prior Publication Data
US 2016/0081939 A1    Mar. 24, 2016

(30) Foreign Application Priority Data

May 6, 2013  (EP) .................................. 13166611
May 27, 2013  (EP) .................................. 13169368

(51) Int. Cl.
*A61K 9/50* (2006.01)
*A61K 9/00* (2006.01)
(Continued)

(52) U.S. Cl.
CPC ............ *A61K 9/501* (2013.01); *A61K 9/0056* (2013.01); *A61K 9/2013* (2013.01); *A61K 9/2813* (2013.01); *A61K 9/2846* (2013.01); *A61K 9/2893* (2013.01); *A61K 9/4858* (2013.01); *A61K 9/5026* (2013.01); *A61K 9/5089* (2013.01); *A61K 31/138* (2013.01); *A61K 31/155* (2013.01); *A61K 31/404* (2013.01); *A61K 31/44* (2013.01); *A61K 31/506* (2013.01);
(Continued)

(58) Field of Classification Search
None
See application file for complete search history.

(56) References Cited

U.S. PATENT DOCUMENTS 6,106,861 A     8/2000  Chauveau et al.
2001/0051188 A1*  12/2001  Ullah ................... A61K 9/1652
                                              424/493

(Continued)

FOREIGN PATENT DOCUMENTS

EP    1157690    11/2001
EP    1759692    3/2007
(Continued)

OTHER PUBLICATIONS

Grace Discovery Sciences, "Syloid® FP Silica Pharmaceutical Excipient", Application Note M391, www.discoverysciences.com (Sep. 2011).*

Primary Examiner — Bethany P Barham
Assistant Examiner — Barbara S Frazier
(74) Attorney, Agent, or Firm — Occhiuti & Rohlicek LLP (57) ABSTRACT

Described herein are oral pharmaceutical formulations comprising a core component and a coating composition applied on the core component. Also described is a process for producing said oral pharmaceutical formulations.

16 Claims, 5 Drawing Sheets

(51) Int. Cl.
*A61K 31/138* (2006.01)
*A61K 31/5415* (2006.01)
*A61K 31/551* (2006.01)
*A61K 31/404* (2006.01)
*A61K 31/517* (2006.01)
*A61K 31/44* (2006.01)
*A61K 9/28* (2006.01)
*A61K 31/155* (2006.01)
*A61K 31/506* (2006.01)
*A61K 9/20* (2006.01)
*A61K 9/48* (2006.01)

(52) U.S. Cl.
CPC ........ *A61K 31/517* (2013.01); *A61K 31/5415* (2013.01); *A61K 31/551* (2013.01)

(56) References Cited

U.S. PATENT DOCUMENTS

| | | | | |
|---|---|---|---|---|
| 2002/0040063 | A1* | 4/2002 | Chandran | A61K 9/0095 514/635 |
| 2005/0287211 | A1* | 12/2005 | Yoshida | A61K 9/2077 424/469 |
| 2008/0248111 | A1 | 10/2008 | Chaudhari | |
| 2011/0223247 | A1* | 9/2011 | Park | A61K 9/0056 424/462 |

FOREIGN PATENT DOCUMENTS

| | | |
|---|---|---|
| WO | 2008/015220 | 2/2008 |
| WO | 2010/046933 | 4/2010 |

* cited by examiner

ORAL PHARMACEUTICAL FORMULATION

CROSS REFERENCE TO RELATED APPLICATIONS

This application is a U.S. National Stage Application of International Application No. PCT/EP2014/059249, filed on May 6, 2014, which claims priority to European Application No. 13166611.7, filed on May 6, 2013, and European Application No. 13169368.1, filed on May 27, 2013, the contents of which are hereby incorporated by reference in their entirety.

The present invention relates to oral pharmaceutical formulations comprising at least one core component and a coating composition applied on the core component. The present invention further is directed to a process for producing said oral pharmaceutical formulation.

BACKGROUND OF THE INVENTION

Although compressed tablets are among the most popular drug dosage forms, some patients, in particular geriatric, pediatric or uncooperative patients, may have difficulties to swallow them. For this reason, orodispersible or orally disintegrating tablets (ODTs) might serve as an alternative dosage form for patients who experience dysphagia. Common among all age groups, dysphagia is observed in about 35% of the general population as well as up to 60% of the elderly institutionalized population.

These problems have been partially addressed by the provision of ODTs that disintegrate in the mouth into smaller pieces allowing easy swallowing. Such tablets need to be strong enough to withstand packaging, transport and subsequent handling without breaking, yet they must be capable of disintegrating gradually when placed into the oral cavity. One regulatory condition explaining what requirements should be met by an ODT is USP method 701 for disintegration. FDA guidance issued in December 2008 stated that ODTs should disintegrate in less than 30 seconds.

Various technologies have been developed that enable the preparation of ODTs, such as spray drying, freeze drying, molding, sublimation, floss formation, direct compression, dry granulation and wet granulation, whereas many of these technologies have proved to be successful only for specific drugs. ODTs are often produced by compressing granules containing at least one active pharmaceutical ingredient (API) together with excipients that trigger dissolving of the tablet in the mouth.

Although a rapid dissolution of the ODT in the oral cavity and absorption through the buccal mucous membrane might be preferred for some APIs, there is a large group of APIs which have an unpleasant taste, smell or cause heartburn or other unfavourable sensation which might lead to a decreased compliance, in particular in pediatric patients. Therefore, coating technologies have been proposed for coating the core components, like granules or pellets, which will be compressed later on to form the final ODT.

WO 2007/036632 corresponding to US 2008/0248111 discloses ODTs of bitter APIs. It is described to use coated granules comprising at least one amine-containing API complexed by low cation-exchange resin and at least one hydrophilic adsorbent, where the mixture of both components is coated with a gastrosoluble polymer. WO 2007/036632 further concerns a method for preparing such granules as well as orodispersible tablets containing such granules. As an example of a gastrosoluble polymer defined as a polymer which dissolves in the stomach at a pH between 1 and 3, Eudragit® E100 is named among others. Furthermore, in one example, it is disclosed to use a mixture of Eudragit® E100 and precipitated silica for coating granules. The weight ratio of the precipitated silica in this coating composition (based on the dry weight of the composition) is about 9.8% by weight. Further, the addition of fatty acids to the coating composition is not disclosed.

EP 1 964 549 A1 further discloses an ODT comprising a fat-soluble API. The ODT is obtained by tableting a mixture of different ingredients adsorbed to an adsorbent. The adsorbent might be selected from the group of calcium silicate, magnesium aluminometasilicate, hydrated silicon dioxide and light anhydrous silicic acid. According to example 1, the weight ratio of hydrated silicone dioxide used is about 55.9% by weight.

EP 1 157 690 concerns a sustained release composition of a core comprising an active ingredient, and a functional coating comprising a gastroresistant polymer and hydrophilic silicon dioxide. A combination of solid fatty acids, silica and a gastro-soluble (meth)acrylate based (co)polymer in the coating is not disclosed.

EP 1 759 692 describes the supply and production of an animal medicine consisting of a substrate in pellet or tablet form, which is attractive to livestock and domestic animals and which consists of yeast or dry animal feed of vegetable or animal origin, in which fine-grained particles of a neutral-tasting, physiologically compatible, solid carrier material are embedded. Said fine-grained particles of carrier material are coated with an active substance for veterinary medicine and said active substance layer is encased with a protective layer of a physiologically compatible polymer matrix. A combination of solid fatty acids, silica and a gastro-soluble (meth)acrylate based (co)polymer in the coating is not disclosed as well.

WO 2010/046933 relates to a pharmaceutical composition of linezolid for oral administration, comprising taste-masked linezolid and at least one pharmaceutically acceptable excipient. The taste-masked linezolid comprises linezolid and at least one taste-masking agent. The pharmaceutical compositions of taste-masked linezolid are suitable for oral administration as suspensions, powders for suspensions, dispersible tablets, orally disintegrating tablets, chewable tablets, effervescent tablets and the like. Combinations of taste-masking coatings comprising solid fatty acids, silica and a gastro-soluble (meth)acrylate based (co)polymer are not disclosed.

WO2008/015220 relates to granules comprising oxycodone, as well as to orally disintegrating tablets including same and optionally acetaminophen. The use of solid fatty acids in a taste-masking coating is not described in this publication.

Generally, in the prior art technologies, hydrated silicas or colloidal silicas were rather used in the formulation of the core component of a pharmaceutical formulation (for example as glidants, as anti-caking agents, as adsorbents) than in coating compositions. Recently, they have been suggested in coating formulations still as anti-caking agents, needed to prevent agglomeration and sticking of the polymer particles during the preparation of the coating dispersion together. Generally, talcum or magnesium stearate are the common choice for these properties.

Figure 8:
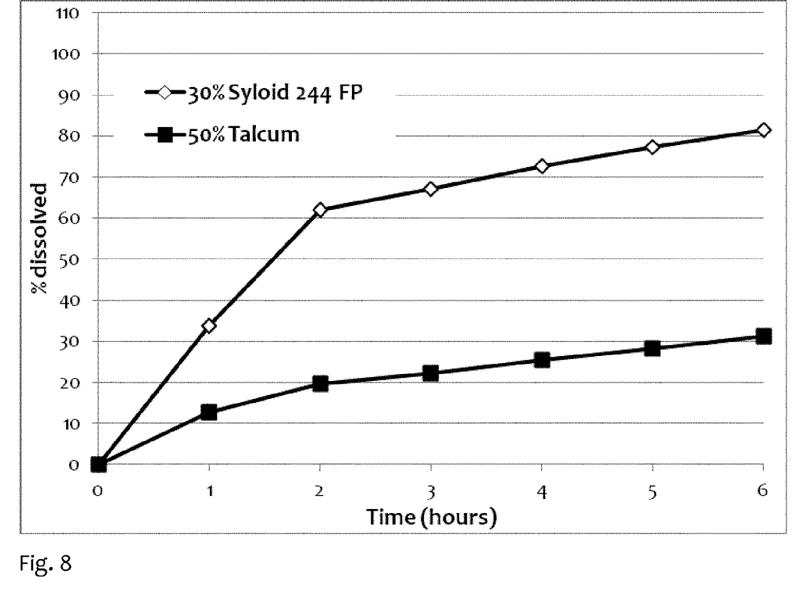
FIG. 8 shows a dissolution profile of pharmaceutical pellets containing phenylpropanolamine and coated with an acrylic polymer intended to sustain the release. One can see that using silica (Syloid 244 FP) increases the release.

Silicas may also impact the release behaviour of the pharmaceutical formulation because they influence the formulation's properties such as hydrophilicity, porosity and swallowability. Generally, in the prior art coatings, silicas are intended to increase the drug release from the formulation (see FIG. 8); Advances in Delivery Science and Technology, Controlled Release in Oral Drug Delivery; Clive G. Wilson, Patrick J. Crowley. (2011); Chapter: Coated Multiparticulates for Controlling Drug Release (p. 269). Moreover, the influence of the use of these silica compounds combined with talcum has been barely investigated, especially in the field of controlled release dosage forms.

Solid fatty acids have been frequently used as auxiliaries in prior art formulations. For example, they find application as glidants in the tableting technology. However, due to their lipophilic and hydrophobic nature, they are not used in applications, where an efficient and rapid dissolution is required in body fluids such as gastric juice.

SUMMARY OF THE INVENTION

In view of the developments made in the prior art so far, the object of the present invention is to provide an oral pharmaceutical formulation with a coating stable in saliva and soluble in gastric juice which, on the one hand, provides a protective coating on core components incorporating at least one API, optionally having unpleasant taste, smell or causing heartburn, and, at the same time, provides a rapid dissolution in the stomach.

Surprisingly, it turned out that the use of silica and solid fatty acids in the coating composition improved the protective efficacy, i.e. led to a delayed delivery of the API(s) in the mouth, but not in the stomach. This is unexpected since the prior art teaches that silicas create hydrophilic networks within the pharmaceutical formulations which enhance the penetration of saliva and thus contribute to a better disintegration and dissolution of the tablet already in the mouth. This is further surprising since the use of fatty acids in certain amounts did not result in a lower dissolution in gastric juice which could have been expected due to their hydrophobic nature.

DESCRIPTION OF FIGURES

The invention will now be described with regard to preferred embodiments shown in the figures. However, the invention is not limited to these preferred embodiments.

DETAILED DESCRIPTION OF THE INVENTION

Definitions:

Any values that are modified by the term "about" in this document generally refer to values that are within an error of two standard deviations from the value according to the applied method, taking into account the measurement conditions and equipment.

All percentages and ratios used therein, unless otherwise noted, are by weight of the total composition, i.e. wt-%, and all measurements have been carried out at ambient or body temperature, i.e. 25° C. or 37° C. respectively, and nominal pressure, unless otherwise noted.

"Solid" means that the product is in a solid state at room temperature (21° C.).

In a first aspect, the present invention is directed to an oral pharmaceutical formulation, comprising
(a) at least one core component, and
(b) a coating composition applied on said at least one core component, characterized in that the coating composition is stable in saliva and soluble in gastric juice and comprises a gastro-soluble(co)polymer, and silica, wherein the amount of silica is 10 to 50 weight-% based on the dry weight of the coating composition.

In a preferred embodiment, the coating composition further comprises a solid fatty acid which is preferably in an amount of 5-10 wt. %, more preferably about 7 wt. %, based on the dry weight of the coating composition; and/or comprises gastro-soluble (meth)acrylate-based copolymers.

The core component of the pharmaceutical formulation of the present invention in a preferred embodiment is selected from the group consisting of crystals, granules, pellets, tablets and mini tablets. However, all conceivable solid pharmaceutical formulations may serve as a core component.

Usually, the core component of the invention further comprises at least one pharmaceutically acceptable auxiliary. The one or more auxiliaries used in the present invention for forming the core components are not particularly limited, and any suitable auxiliary known to the skilled person can be used. Suitable auxiliaries are, for example, corn starch, calcium phosphate, calcium hydrogen phosphate, calcium sulfate, calcium stearate, magnesium stearate, sorbitol, mannitol, gelatine, natural or synthetic gums like carboxymethylcellulose, methylcellulose, alginate, dextran, guar gum, to name a few.

Auxiliaries are well-known to the skilled person, e.g. from the Handbook of Pharmaceutical Excipients, Rowe R C, Sheskey P J, Quinn M E (eds), Pharmaceutical Excipients 5. [CD-ROM] London: Pharmaceutical Press, 2009.

Specific examples of auxiliaries used in the core component of the present invention include, but are not limited to:
Antioxidants like butylated hydroxyanisole and butylated hydroxytoluene
binders like alginic acid, sodium alginate, starch and derivatives thereof, cellulose and derivatives thereof, carboxymethyl cellulose sodium (CMC), microcrystalline cellulose (MCC), dextrin, dextrose, guar gum, lactose, povidone, tragacanth, zein,
colors and pigments,
diluents/fillers, like calcium carbonate, calcium sulfate, microcrystalline cellulose (MCC), powdered cellulose, dextrates, dextrose, dextrin, kaolin, lactose, maltodextrin, mannitol, starch, sucrose,
disintegrants like alginic acid, sodium alginate, microcrystalline cellulose, starch, sorbitol, colloidal silicon dioxide, hydrated silica, croscarmellose sodium, guar gum, sodium starch glycolate, crospovidone,
emollients like glycerin, glyceryl monostearate, isopropyl myristate, polyethylene glycols,
emulsifiers like carbomer, carrageenan, lanolin, lecithin, mineral oil, pectin, sorbitan esters,
flavors,
glidants/antiadherents like talcum or colloidal silicon dioxide,
humectants like glycerin or sorbitol,
lubricants like calcium stearate, magnesium stearate, sodium stearyl fumarate, stearic acid, talcum,
plasticizers like glycerin or triethanolamine,
preservatives like alcohol or sorbic acid,
surfactants like polyethylene glycols,
suspending agents like acacia, agar, kaolin, pectin,
sweeteners like sorbitol, sucrose, dextrose, fructose, mannitol, xylitol.

The silica used in the coating composition of the present invention preferably is selected from porous silica, for example fumed silica, and more preferably from amorphous silica. Preferred examples of silicas for use in the present invention are Syloid® 244 FP and Sylysia® 770.

Syloid® 244 FP is a synthetic amorphous silica appearing as white free flowing powder. It meets the test requirements of the U.S. Pharmacopeia for silicon dioxide and the requirements for E551, specified in the European Commission Directive 2008/84/EC. It is a fine-sized, high pore volume silica gel with a large internal surface area. It is marketed by W.R. Grace & Co.

A further preferred silica is Sylysia® 770, an amorphous, micronized silica having an average particle size of 6.7 μm. The pore volume of Sylysia® 770 is 0.44 ml/g.

Another type of silica or silica derivatives which can be used in the context of the present invention are silica derivatives marketed under the trade name Zeopharm® (J.M. Huber Corporation) and Neusilin® (Fuji Chemical Industry Co., Ltd).

Although hydrophilic silica is preferred in the present invention, it is conceivable to use hydrophobic silica as well.

Talc is a mineral composed of hydrated magnesium silicate having the formula $H_2Mg_3(SiO_3)_4$ or $Mg_3Si_4O_{10}(OH)_2$ and in its loose form known as talcum or talcum powder. Luzenac® Pharma talc (Rio Tinto Minerals Group) is a preferred talcum and further talcums are described in the Handbook of Pharmaceutical Excipients, Rowe R C, Sheskey P J, Quinn M E (eds), Pharmaceutical Excipients 5. [CD-ROM] London: Pharmaceutical Press, 2009.

According to the present invention, silica is used in the ratio of about 10 to 50 wt-% based on the dry weight of the coating composition. Should a mixture of silica and talcum be used, then the weight ratio of the two ingredients to each other may vary from about 90:10 to 10:90 between silica and talcum.

Generally, it is preferred that the coating composition of the present invention contains talcum in an amount of about 15 to 40 wt-% based on the dry weight of the coating composition.

The weight ratio of the coating composition to the core component (in terms of dry weight percentages) is between about 5 to 50 wt-% of the weight of the core component. A preferred weight range for the coating composition in dry form is between about 10 and 30 wt-%.

The present invention includes one or more APIs in the core component, which should be protected from being immediately dissolved in the oral cavity (i.e. saliva). For example, the API may have an unpleasant taste, smell or may cause heartburn.

According to the biopharmaceutical classification system, the APIs are classified in function of their aqueous solubility and their intestinal permeability which depends on their lipophilic affinity with the cell membrane (Wu et al. Predicting Drug Disposition via Application of BCS: Transport/Absorption/Elimination Interplay and Development of a Biopharmaceutics Drug Disposition Classification System; Pharmaceutical Research, Vol. 22, No. 1, January 2005) as follows:
Class I: High solubility—high permeability
Class II: Low solubility—high permeability
Class III: High solubility—low permeability
Class IV: Low solubility—low permeability Regarding this classification one can consider as hydrophilic APIs the highly soluble APIs (Class I & Class III), and as hydrophobic APIs the poorly soluble APIs (Class II & Class IV). We have then found that the present invention works well with all APIs of these classes including Class III (for example Metformin) and with Class II (for example Imatinib), meaning that the film coating containing the silica or silica/talcum is able to delay the delivery of an API in the mouth, even if the API is hydrophilic or hydrophobic.

Such APIs might be selected from Abacavir, Acyclovir, Nelfinavir, Inidnavir, Ribonavir, Saquinavir, Ganciclovir, Tamoxifen, Paracetamol, Nifedipin, Nifurtimox, Carbamazepin, Codeine, Dihydrocodeine, Hydrocodone, Hydromorphone, Methadone, MethylNatrexone, Morphine, Nalbuphine, Nalfurafin, Nalmefan, Naltrexone, Oxycodone, Oxymorphone, Fentanyl, Pentazocin, Pethidine, Tapentadol, Tilidin, Tramadol, Metformin, Imatinib, Sorafenib, Axitinib, Crizotinib, Dasatinib Erlotinib, Fostamatinib, Gefitinib, Lapatinib, Lenvatinib, Mubritinib, Nilotinib, Pazopanib, Ruxolitinib, Sunitinib, Vandetanib, Vemurafenib Cephalosporines, Loratidine, Olanzapine, Piroxicame, or Diphenhydramine, or mixtures thererof.

The further component of the coating composition according to the present invention is a gastro-soluble (co)polymer comprising (meth)acrylate-based copolymers. Those polymers are readily available in the market and might be selected from the group consisting of Eudragit® EPO, Kollicoat® Smartseal 30D; further polymers useful in the present invention are Eudragit® E100, and Eudragit® E12,5.

In the oral formulation according to the present invention, the weight ratio of silica to the gastro-soluble(co)polymer preferably is about 10:90 to 60:40 wt-%. However, usually a weight ratio between silica or silica/talcum to the gastro-soluble (co)polymer of between about 10:90 to 50:50 wt-% is most preferred.

Further, the absolute amount of the gastro-soluble (co)polymer is about 30 to 90 wt-% based on the dry weight of the overall coating composition. A preferred weight percentage of the gastro-soluble (co)polymer is about 40 to 70 wt-% based on the dry weight of the coating composition.

In a preferred embodiment, the oral formulation of the present invention is in the form of a dispersible tablet, preferably an orodispersible tablet (ODT), which is formed by a compression of granules coated with the coating composition of the present invention. Regarding general techniques of manufacturing oral pharmaceutical compositions of the present invention, it is referred to Remington, The Science and Practice of Pharmacy, $22^{nd}$ edition, 2012, chapter 45 "Oral solid dosage forms".

The formulation of the present invention preferably contains solid fatty acids selected from C10-C20 unsaturated fatty acids or mixtures thereof. In a most preferred aspect, the fatty acid is stearic (C18) and/or palmitic acid (C16).

Fatty acids as defined herein are carboxylic acids derived from or contained in an animal or vegetable fat or oil. Fatty acids are composed of a chain of alkyl groups and are characterized by a terminal carboxyl group. Solid fatty acids further useful in the present invention include, but are not limited to, hydrogenated palm kernel oil, hydrogenated peanut oil, hydrogenated palm oil, hydrogenated rapeseed oil, hydrogenated rice bran oil, hydrogenated soybean oil, hydrogenated sunflower oil, hydrogenated castor oil, hydrogenated cottonseed oil, and the like, and mixtures thereof. Other fatty acids include, for example, decenoic acid, docosanoic acid, lauric acid, myristic acid, and the like, and mixtures thereof.

According to the present invention, it turned out that a combination of silica and solid fatty acid in the coating leads to an unexpected release behaviour of the pharmaceutical formulation: in contrast to what could have been expected, silica effectively avoids the sensation of unpleasantly tasting API's in the mouth within a time frame of the expected retention time of the formulation in the mouth (up to about 5 minutes). Further, the addition of a solid fatty acid such as stearic acid in a suitable amount supports this effect, but surprisingly does not deteriorate the release of the API in the gastric juice.

Figure 2:
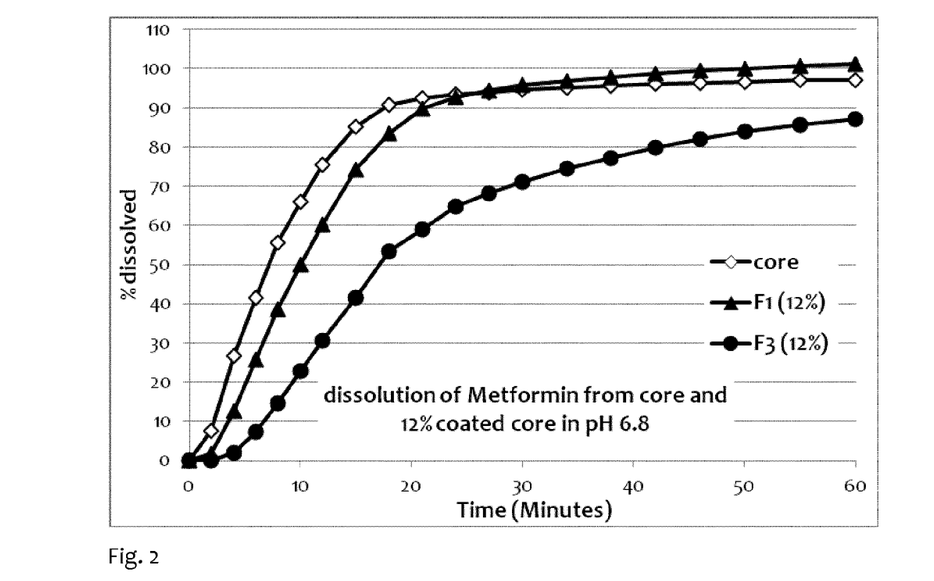
FIG. 2 shows the dissolution profile of a pharmaceutical composition comprising Metformin in the core component and coatings of stearic acid and silica; a comparison is shown between coated and uncoated compositions dissolved at pH 6.8; one can see that coated compositions which is not containing silica (F1) show worse characteristics over coated compositions comprising a mixture of silica and stearic acid (F3) in the dissolution profile at pH 6.8.

It is referred to FIG. 2 showing the dissolution profile of a pharmaceutical composition comprising Metformin in the core component and coatings of Eudragit EPO, stearic acid and silica; a comparison is shown between coated and uncoated compositions dissolved at pH 6.8; one can see that coated compositions which are only containing stearic acid (and no silica) (F1) already show better release behaviour than uncoated cores. However the coated compositions comprising a mixture of silica and stearic acid (F3) show the best dissolution profile at pH 6.8.

Usually, the process used to manufacture orodispersible tablets includes compression tableting, a process which is not very different from the manufacturing method used for traditional tablets. However, ODTs usually are compressed at a much lower compression force than traditional tablets. Due to this lower compression forces and the resulting characteristics of the tablet core component, problems such as material sticking during manufacture can appear. Therefore, usually lubricants such as magnesium stearate are added to the blend to reduce the amount of material that may stick to the devices used. Further ingredients for use in ODTs are disintegrants, such as crospovidone, microcrystalline cellulose, croscarmellose, starch, sodium starch glycolate, L-HPC, mannitol, colloidal silicon dioxide, hydrated silica and/or hypromellose.

In a preferred embodiment, the oral formulation of the present invention may contain at least one co-processed excipient as disintegrants, for example but not limited to Prosolv® ODT, Panexcea® ODT, F-Melt®, Pharmaburst®, Ludiflash®, or mixtures thereof.

In a second aspect, the present invention is directed to a process for producing an oral pharmaceutical formulation as described hereinabove, comprising (a) providing at least one core component comprising at least one API;

(b) providing a solution or suspension of a coating composition, which comprises a gastro-soluble (meth)acrylate based (co)polymer and silica in an amount of 10 to 50 wt-% based on the dry weight of the coating composition and a suitable amount of a solid fatty acid;

(c) applying the solution of suspension to the core component; and (d) drying in order to provide a solid coating composition that is stable in saliva and soluble in gastric juice.

Preferably, the solid fatty acid is present in an amount of 5-10 wt %, more preferably about 7 wt-%, based on the dry weight of the coating composition.

Regarding coating technologies for use in the present invention, it is also referred to the above mentioned chapter 45 of Remington, The Science and Practice of Pharmacy.

The oral pharmaceutical formulation might be used as such or may be further subjected to manufacturing steps, for example to prepare an ODT from the coated particles.

While the present invention has been described with reference to preferred embodiments thereof, it will now be described in more detail with reference to the following examples, which, however, do not limit the scope of the invention.

EXAMPLES

Granules were manufactured using the wet granulation process, using water as granulation liquid. This step was achieved in high shear mixer or in fluid bed equipment's regarding the API investigated.

All the coating dispersions were prepared as described in the literature, such as in the EUDRAGIT® E PO quick start technical information from Evonik Industries AG, silica was added at the same step as the talcum.

Coating process was done in Glatt fluid bed WSG3.1 with the wurster equipment. Same parameters were applied for the coatings with and without silica or silica/talcum. Drug dissolution in the mouth and in the stomach has been investigated with dissolution tests in pH 6.8 and pH 1.0, respectively.

The in vitro release investigations were carried out by USP release method with apparatus 2 (Paddle) for tablets and for hard capsules. Hard capsules were filled with granules and placed into appropriate sinkers. Tests were conducted at a temperature of 37° C. The speed of rotation of the stirrer was 75 rpm in 900 mL of a phosphate buffer solution for pH 6.8 and of HCl 0.1 N for pH 1.0.

Example 1

Tablet core components of Metformin were manufactured according to the following composition:

| Composition | Batch 1202E005 [%] |
|---|---|
| Granulate | |
| Metformin HCl | 49.98 |
| Microcryst. Cellulose | 40.61 |
| Hypromellose 6 mPA · S | 3.70 |
| Croscarmellose Na | 5.71 |
| Total for inner phase | 100.0 |
| Outer phase for tablets | |
| Granulate | 99.1 |
| Aerosil 200 | 0.5 |
| Magnesium stearate | 0.4 |
| Total | 100.0 |

Granules were made from the inner phase mixture, the external phase was added to the dried granules and mixed during 3 minutes. The final blend was compressed to tablets using 8 mm, round, biconvex punches, the resulting tablet weight was 170 mg.

The tablet core components were coated with the following compositions:

| | F1 [%] | F2 [%] |
|---|---|---|
| Eudragit EPO | 11.42 | 10.79 |
| Sodium Lauryl Sulfate | 1.14 | 1.08 |
| Stearic Acid | 1.71 | 1.62 |
| Talcum | 5.71 | 5.39 |
| Sylysia 770 | 0.00 | 1.08 |
| Color | 0.02 | 0.04 |
| Water | 80.00 | 80.00 |
| Total | 100.00 | 100.00 |

F1 corresponds to a classical coating composition as described in the EUDRAGIT® E PO quick start technical information from Evonik Industries AG.

Figure 1:
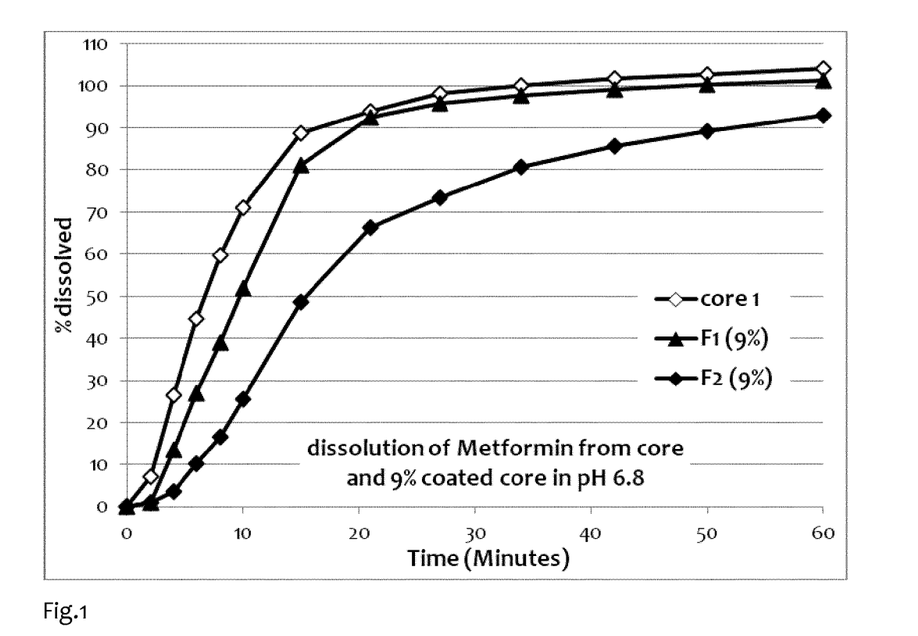
FIG. 1 shows a dissolution profile of pharmaceutical compositions containing Metformin at a pH of 6.8; as it can be seen, compositions comprising silica and stearic acid (F2) have a decreased dissolution of Metformin at a pH of 6.8 in view of classical compositions (F1)

According to FIG. 1, the delivery in mouth simulated conditions was readily improved with the incorporation of Sylysia® 770 as permeabilizing agent, even at 9% coating. Thus, formulation F2 effectively delays the release of Metformin from the formulation in the oral cavity.

Example 2

Example 2 uses the same core component composition as in Example 1. The coating composition was as follows:

| | F3 [%] |
|---|---|
| Eudragit EPO | 8.30 |
| Sodium Lauryl Sulfate | 1.08 |
| Stearic Acid | 1.50 |
| Talcum | 5.20 |
| Syloid 244 FP | 3.40 |
| Color | 0.04 |
| Water | 80.48 |
| Total | 100.00 |

In F3, Syloid® 244FP was used as the permeabilizing agent, at 12% coating.

FIG. 2 shows that even at 12 wt-% coating, the delivery was improved when incorporating Syloid 244FP at a ratio of 40 wt-%.

Figure 3:
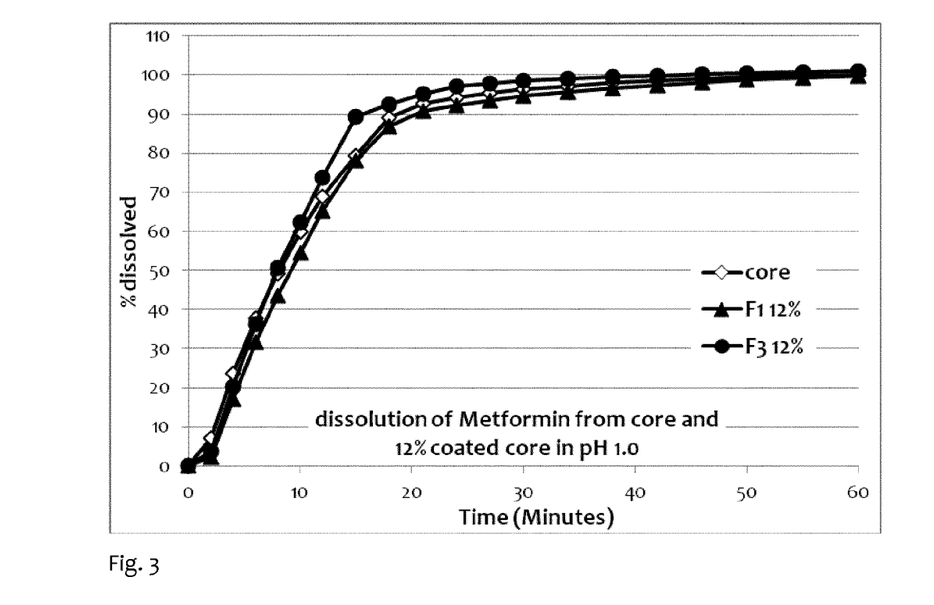
FIG. 3 shows a comparison between coated and uncoated compositions containing Metformin, at pH 1.0; all compositions show the same dissolution behaviour.

Although different porous silica investigated exhibited some little differences, the dissolution profiles at pH 1.0 were very close to the uncoated formulation (core component), see FIG. 3. All the formulation showed an immediate release in the stomach simulated conditions (pH 1.0).

Example 3

As core components, granules of Imatinib were manufactured according to the following formulation:

| Composition | Batch 1219E001 [%] |
|---|---|
| Granulate | |
| Imatinib Mesylate | 81.29 |
| Microcryst. Cellulose | 17.01 |
| Hypromellose 5 mPA · S | 1.70 |
| Total for inner phase | 100.0 |

The granules were coated according to the following formulation:

| Composition | Im1 [%] | Im3 [%] | Im4 [%] |
|---|---|---|---|
| Eudragit EPO | 11.70 | 11.70 | 11.70 |
| Sodium Lauryl Sulfate | 1.17 | 1.17 | 1.17 |
| Stearic Acid | 1.75 | 1.75 | 1.75 |
| Talcum | 5.83 | — | 5.83 |
| Syloid 244 FP | — | 5.83 | 4.7 |
| Color | 0.01 | 0.01 | 0.04 |
| Water | 79.54 | 79.54 | 74.81 |
| Total | 100.00 | 100.00 | 100.00 |

Coating was achieved with 12 wt-% and 30 wt-%. The in vitro release investigations were carried out as previously described. Granules were put into hard capsules and sinkers were used.

Figure 4:
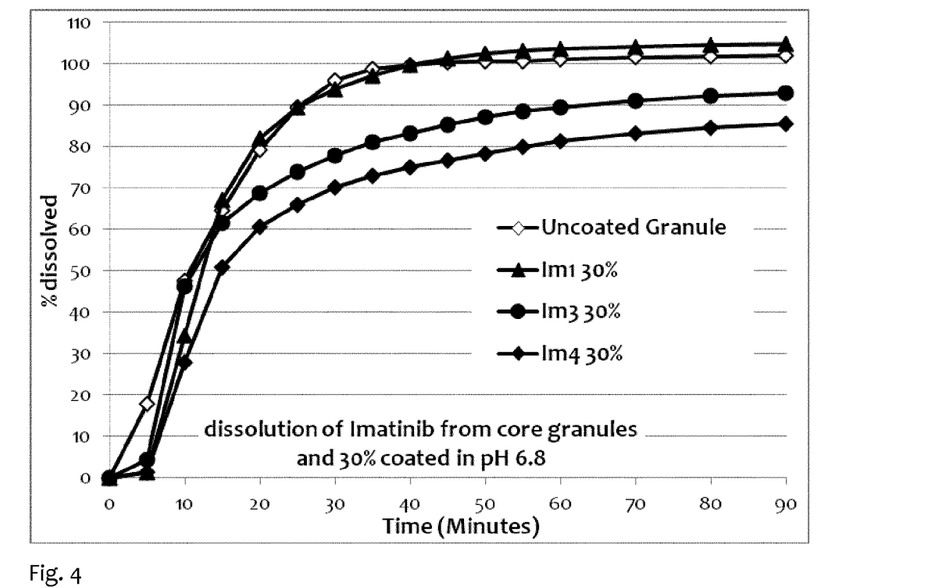
FIG. 4 shows the dissolution profile of Imatinib from core granules compared between coated and uncoated granules at pH 6.8. The delay of the release is clearly better when coating compositions according to the invention are used (IM3/IM4) versus a classical coating composition not falling under the present invention (IM1)

As it can be seen from FIG. 4, adding the porous silica improved the taste masking compared to the classical coating formulation, particularly in combination with talcum.

Figure 5:
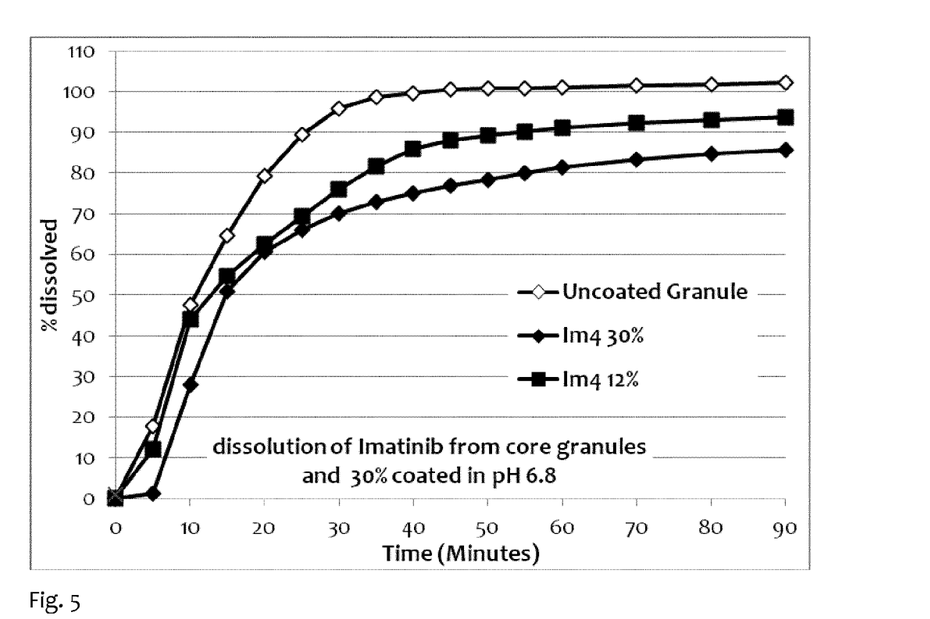
FIG. 5 shows the dissolution profile at pH 6.8 of Imatinib from core granules, 12 wt.-% and 30 wt.-% coated granules. One can see that the coating compositions according to the present invention (IM3/IM4) clearly have an improved dissolution profile with both, 12 and 30 wt.-% coatings.
Figure 6:
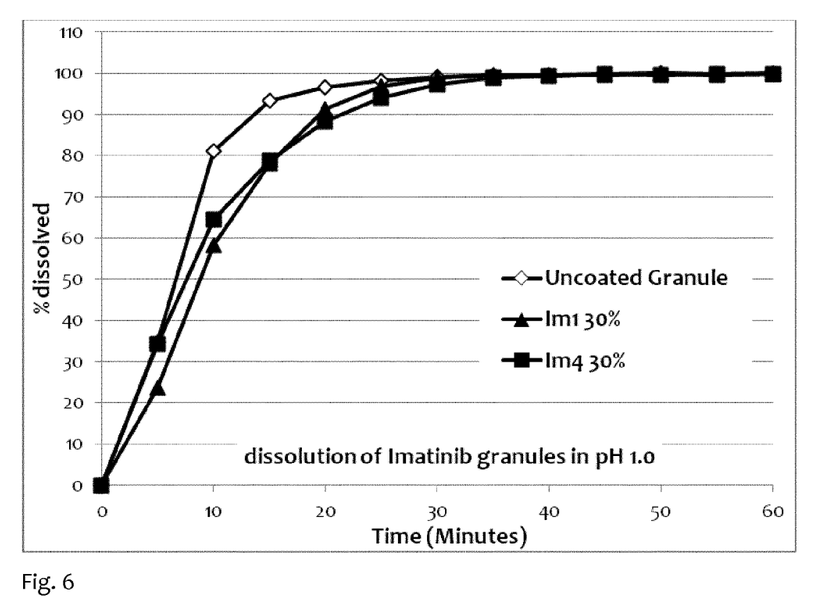
FIG. 6 shows a dissolution profile of Imatinib granules in pH 1.0. As it can be seen, the dissolution profiles in the stomach simulated medium are quite similar between coated and uncoated granules as desired.

Adding the porous silica and talcum improved the taste masking compared to the classical coating formulation with only 12% coating, but even more with 30% coating (FIG. 5). All of the formulations show an immediate release in the stomach simulated conditions (pH 1.0; see FIG. 6).

Example 4

ODTs were manufactured from 30% coated Im4 granules, the composition was as follows:

| Tablet Composition | [%] |
|---|---|
| Coated Granules (Im4 30%) | 54.60 |
| Panexcea ODT | 41.00 |
| Crosscarmelose NA | 3.00 |
| Sodium Stearyl Fumarate | 1.40 |
| Total | 100.0 |

Tablet weight: 700 mg,
Hardness: 60-80 N
Diameter: 15 mm

Figure 7:
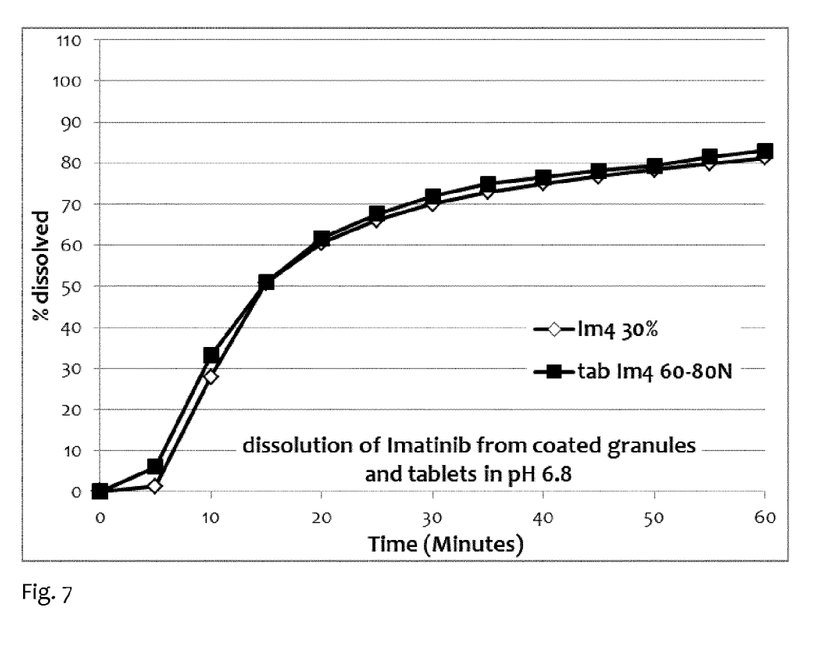
FIG. 7 shows the dissolution profile at pH 6.8 of Imatinib from 30 wt.-% coated granules (IM4) and from fast disintegrating tablets made from these granules (tab IM4). The dissolution profiles are quite similar, especially after 15 minutes.

One can see in FIG. 7 that the dissolution profiles exhibit the same shape. During the first 15 minutes, the tablets deliver the API slightly more rapidly but thereafter the dissolution profiles are quite similar.

Therefore, the composition according to the invention shows an improved protective effect for coated granules but also for ODTs, meaning that the coating film resists to the compression, due to an improved flexibility.

The invention claimed is:

1. An oral pharmaceutical formulation, comprising
   a) at least one core component, and
   b) a coating composition applied on said at least one core component, wherein the coating composition is stable in saliva and soluble in gastric juice and comprises a gastro-soluble (meth)acrylate based (co)polymer, silica in an amount of 10-50 wt-% based on the dry weight of the coating composition, and a solid fatty acid, wherein the solid fatty acid is present in an amount of 7-10 wt-% based on the dry weight of the coating composition and the solid fatty acid is stearic or palmitic acid or a mixture of stearic and palmitic acid.

2. The formulation of claim 1, wherein the core component is selected from the group consisting of crystals, granules, pellets, tablets and minitablets.

3. The formulation of claim 1, wherein the silica is a porous silica.

4. The formulation of claim 3, wherein the porous silica is hydrophilic.

5. The formulation of claim 1, wherein the core component comprises an active pharmaceutical ingredient (API) that has an unpleasant taste or smell or causes heartburn.

6. The formulation of claim 1, wherein the core component comprises an active pharmaceutical ingredient selected from the group consisting of metformin, imatinib, sorafenib, erlotinib, lapatinib, sunitinib, cephalosporines, loratidine, olanzapine, piroxicame, and diphenhydramine.

7. The formulation of claim 1, wherein the weight ratio of the silica to the gastro-soluble (meth)acrylate based (co)polymer is 10:90 to 60:40.

8. The formulation of claim 7, wherein the amount of the gastro-soluble (meth)acrylate based (co)polymer is 30-90 weight %, based on the dry weight of the coating composition.

9. The formulation of claim 1, wherein the coating composition further comprises talcum.

10. The formulation of claim 1, wherein the amount of the coating is 5-50% of the weight of the core component.

11. The formulation of claim 1, wherein the formulation is in the form of a dispersible tablet comprising compressed granules coated with the coating composition.

12. The formulation of claim 4, wherein the hydrophilic silica is a fumed silica.

13. The formulation of claim 9, wherein the talcum is present in the amount of 15-40 weight % based on the dry weight of the coating composition.

14. The formulation of claim 1, wherein the amount of the coating is 10-30% of the weight of the core component and/or the solid fatty acid is present in an amount of about 7 wt-% based on the dry weight of the coating composition.

15. A process for producing an oral pharmaceutical formulation that is stable in saliva and soluble in gastric juice, the process comprising
   a) providing at least one core component comprising at least one API;
   b) providing a solution or suspension of a coating composition, comprising a gastro-soluble (meth)acrylate based (co)polymer, silica in an amount of 10-50 wt-% based on the dry weight of the coating composition, and a solid fatty acid, wherein the solid fatty acid is present in an amount of 7-10 wt-% based on the dry weight of the coating composition and the solid fatty acid is stearic or palmitic acid or a mixture of stearic and palmitic acid;
   c) applying the solution or suspension to the core component; and
   d) drying the core component to which the solution or suspension was applied, thereby producing an oral pharmaceutical formulation that is stable in saliva and soluble in gastric juice.

16. The process of claim 15, wherein one or more coated core components are compressed into a dispersible tablet.

* * * * *